United States Patent [19]

Bussière et al.

[11] Patent Number: 4,716,296
[45] Date of Patent: Dec. 29, 1987

[54] APPARATUS FOR CURING DENTAL RESTORATIVE COMPOSITES

[75] Inventors: Ronald L. Bussière, Edmonds; Robert J. Smith, Lynnwood, both of Wash.

[73] Assignee: Surgicorp, Lynnwood, Wash.

[21] Appl. No.: 371,610

[22] Filed: Apr. 26, 1982

[51] Int. Cl.$^4$ ............................................. H01J 61/40
[52] U.S. Cl. .......................... 250/504 H; 250/504 R
[58] Field of Search ................ 250/504, 504 H, 504 R

[56] References Cited

U.S. PATENT DOCUMENTS 4,149,086  4/1979  Nath .................................. 250/504

OTHER PUBLICATIONS

*The Illustrated Encyclopedia of Science and Technology,* 1979, p. 228.
Exhibit 1—Consists of a portion of a brochure distributed by Kulzer, Inc. advertising a dental composite curing unit sold under the trade name TRANSLUX.
Exhibit 2—Consists of a portion of a Dentsply International Inc. advertising brochure for an apparatus for curing dental restorative composites distributed under trade name PRISMA-LITE.
Exhibit 3—Avertisement for an apparatus for curing dental restorative composites manufactured by Vivadent, Inc. and sold under the trade name HELIOMAT.
Exhibit 4—Avertisement for an apparatus for curing dental composites sold under the brand name ESPE--Premier.
Exhibit 5—Illustrates a dental restorative composite curing apparatus sold under the mark DenMat.
Exhibit 6—Brochure advertising a visible light curing unit sold under the mark POLY-LITE 2000.
Exhibit 7—Advertisement for versatile light system manufactured by the Litema Company of W. Germany.
Exhibit 8—Advertisement for an apparatus for curing dental restorative composites manufactured by Demetron Research Corporation and sold under the mark ULTRA NOVAR.
Exhibit 9—Portions of an advertising brochure distributed by OCLI concerning color separation dichroic filters.
Exhibit 10—Composed of the title page and pp. 749-753 of textbook entitled *Organic Chemistry of Synthetic High Polymers,* by Robert W. Lenz.
Exhibit 11 includes pp. 155-159 of *Polymer Science and Engineering,* by David J. Williams.
Exhibit 12—pp. 1, 2, 4 and 50 of text entitled *Applications of Absorption Spectroscopy of Organic Compounds,* by John R. Dyer.

Primary Examiner—Craig E. Church
Assistant Examiner—Jack I. Berman
Attorney, Agent, or Firm—Christensen, O'Connor, Johnson & Kindness

[57] ABSTRACT

An apparatus for applying light in selective frequency ranges to organic composite materials used in restorative dentistry for optimum curing of the composite materials includes a lamp (14) energized by power supply (12) to transmit light through a flexible light transmitting cord (22). A dichroic filter lens (18) is disposed within an end cap (32) detachably securable to the end of a contra angle probe (27) mounted on a hand held handle (28) secured to the end of cord (22) opposite lamp (14). Lens (18) is selected with reference to the particular composite material to be cured so that substantially all frequencies of light produced by lamp (14) are blocked or attenuated except the frequency range which produces uniform and complete curing of the composite material without causing radical cross-linking of the composite material. The desired light frequency range is ascertained by sequentially directing different frequencies of light at a sample of the composite material and measuring the intensity of the light absorbed by the compound at each test frequency. The frequencies of light which are highly absorbed by the organic material without causing radical cross-linking of the material are chosen for the curing process.

6 Claims, 3 Drawing Figures

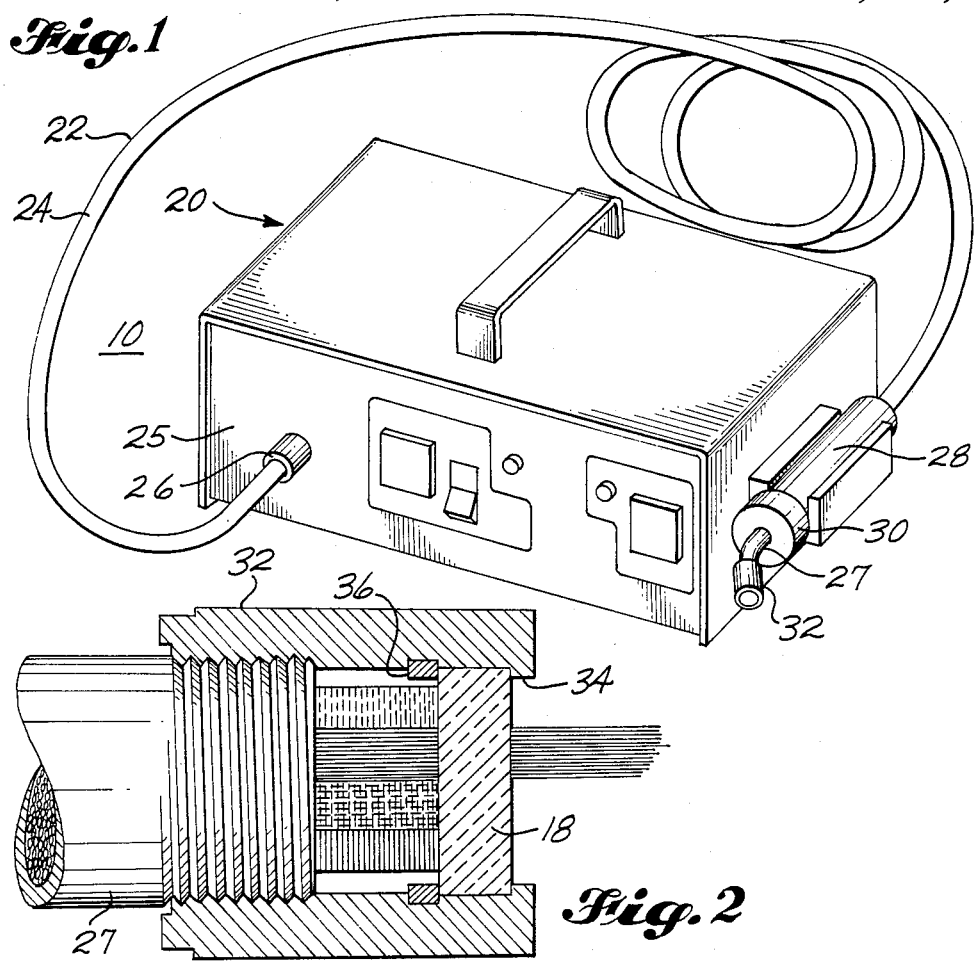
Fig. 1
Fig. 2
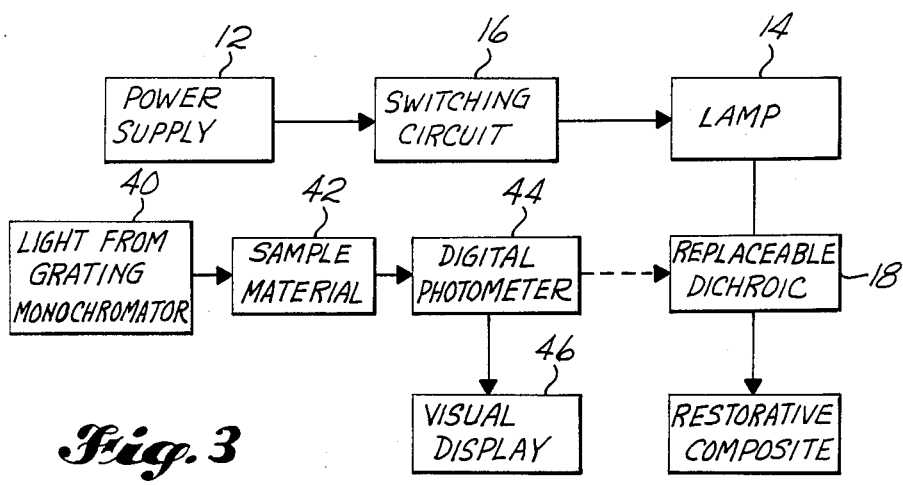
Fig. 3

APPARATUS FOR CURING DENTAL RESTORATIVE COMPOSITES

TECHNICAL FIELD

The present invention relates to a method and apparatus for curing organic restorative composites used to repair teeth and more particularly to optically curing the restorative composite by directing an optimum frequency range of light at the composite.

BACKGROUND ART

In the past dentists used primarily gold or silver alloys to fill or otherwise repair teeth. Other less expensive restorative materials are now being used as substitutes for silver and gold. These newer restorative materials also have the advantages of matching the color of a patient's teeth and being highly durable. Typically the newer materials are a composite of an organic bonding agent and an inorganic filler material. The composite material is applied to the patient's tooth in thin layers and then cured by applying light of a proper frequency. The optimum light frequency range for rapid and uniform curing of the material depends on the specific composition of the material.

Known apparatus for curing dental repair composites typically include a light bulb disposed within a housing and a switch for interconnecting the light bulb with standard alternating current from a wall socket. A flexible cord composed of fiber optic strands directs the light from the bulb to the patient's tooth.

Some known types of light curing units produce light in a wide range of frequencies far beyond that required for rapidly and completely curing the specific restorative materials being used. The additional frequencies of light can actually hinder the effective grafting together of the polymer and monomer which compose the bonding agent of the composite.

Higher frequencies of ultraviolet light, especially below 300 nanometers, cause radical cross-linking of the organic molecules of the restorative composite resulting in instability of the composite. Consequently, the composite breaks down over time. Also, clinical studies have shown that higher frequency ultraviolet rays can cause damage to gum tissue. Thus, it is important that these frequencies of ultraviolet light produced by light curing units be attenuated.

Wavelengths of light not absorbed during the curing of restorative composites, especially those above 700 nanometers, generate substantial amounts of heat. This heat can cause a thin outer shell to form on the composite material so that the oxides created during the curing process are not able to flash off of the composite material. As a result, the interior portions of the composite material may not fully cure, resulting in premature failure of the restorative material.

Also, the light produced by known light generating units often is not intense enough to penetrate very deeply into composite materials. As a consequence, these materials must be applied in very thin layers, thereby increasing the time required to complete a filling or perform the dental work. The lack of light intensity in part may be due to the inefficiency of the filter or other means, if any, used to control the frequency of the light produced by the unit.

Thus, it is a primary object of the present invention to overcome the shortcomings of known curing light generating systems discussed above. The present invention provides a method for determining the proper frequency range of light for optimally curing organic restorative dentistry composites. Further, the present invention provides an apparatus which is capable of producing high intensity light in the precise frequency range which has been found by the present method to cure the particular composite material utilized to repair the tooth while attenuating or minimizing harmful or unwanted frequencies of light.

DISCLOSURE OF THE INVENTION

The present invention relates to a method and apparatus for photochemically curing organic restorative composites used to repair teeth. The method includes ascertaining the particular light frequency range which is absorbed by the restorative composite during optimum curing and then manufacturing a dichroic lens to attenuate substantially all frequencies of light except the particular frequency range which produces proper curing of the composite. The dichroic lens is interposed between a light source and the composite being cured.

The method for ascertaining which frequency range of light optimally cures a specific restorative composite includes using a grading monochromator to direct light of individual frequencies at a sample of the compound. A photometer is employed to analyze the frequencies of light which are highly absorbed by the compound since these frequencies correspond to the frequencies at which the polymerization cycle occurs in the composite. The amount of light absorbed at different light frequencies may be recorded on various instruments such as on a strip chart recorder. By this method, the precise frequency range at which any specific restorative composite is cured may be conveniently and accurately determined.

The apparatus used for applying light to the restorative composite at the ascertained optimum frequency range includes a halogen lamp which is interconnected with a power supply by an appropriate switching circuit to energize and deenergize the lamp when desired. The light from the lamp is transmitted to a patient's tooth through a flexible light cord composed of fiber optic strands. A contra angle probe is mounted on a handle attached to the free end of the light cord to enable the operator to accurately direct the light to the desired location in the patient's mouth.

The light from the lamp is frequency filtered by a dichroic filter lens mounted within the probe at the end of the light cord. The lens blocks unwanted light and only permits light of the desired frequency range to reach the patient's tooth. Light which may be harmful to the patient, such as in the near infrared and ultraviolet range, or light which hinders curing, is attentuated by the lens. The dichroic lens is very efficient in that it attenuates very little of the light of the desired band width produced by the lamp.

The dichroic filter lens, which is generally circular in shape, is mounted within the interior of a cap having internal threads for attachment to the end of the probe. The lens is held in place by a backing ring pressed within the hollow interior of the cap. This mounting arrangement securely retains the lens within the probe cap while permitting the lens to be conveniently replaced when, for instance, a different restorative composite requiring different light frequencies for optimum curing is being used to repair a patient's tooth.

BRIEF DESCRIPTION OF THE DRAWINGS

The details of one typical embodiment of the present invention will be described in connection with the accompanying drawings, in which:

FIG. 1 is a pictorial view of a light generating apparatus of the present invention, specifically illustrating a housing, light cord and probe;

FIG. 2 is an enlarged fragmentary view of the probe tip of the present invention particularly illustrating the dichroic filter lens; and FIG. 3 is a block diagram of a method of the present invention for photochemically curing restorative organic compounds used to repair teeth.

BEST MODE OF THE INVENTION

Referring initially to FIG. 3, a frequency regulated light generating apparatus 10 constructed according to the best mode of the invention currently known to applicant includes a power supply 12 for energizing a lamp 14. A switching circuit 16 is interposed between power supply 12 and lamp 14 to energize the lamp to a high intensity or operating level and then deenergize lamp to either a standby or off state. Various types of known switching circuitry may be used to accomplish this function. The output light from lamp 14 is filtered by a filter lens 18 prior to the light being directed to the composite material being cured.

Power supply 12 may be in the form of a standard 110 volt, 60 hertz alternating current source. Alternatively, the power may be supplied from a 220 volt, 50 hertz alternating current source. A transformer, not shown, may be used to reduce the source voltage to the operational level of lamp 14, typically in the range of 10 to 20 volts.

As discussed above, switching circuit 16 is used to selectively energize and deenergize lamp 14. Switching circuits of the type required for energizing lamp 14 are well known. Neither power supply 12 nor switching circuit 16 form part of the present invention.

Referring additionally to FIG. 1, lamp 14 is located within a rectangular-shaped housing 20 which also houses switching circuit 16 and the remainder of the electrical components of apparatus 10. Lamp 14 is preferably of a type which is capable of producing high intensity light in the near ultraviolet range, such as a quartz halogen type. However, other types of lamps may be employed without departing from the scope of the present invention.

The light generated by lamp 14 is transmitted to the patient's mouth by a flexible light cord 22. Cord 22 is preferably composed of a plurality of very small diameter fiber optic strands, not shown, covered with an outer plastic jacket 24. The fiber optic strands may be sheathed by a metal armored cable, not shown, which in turn is covered with the outer plastic jacket 24. One end of cord 22 is connected in light transmission communication with lamp 14 by engaging the end of the cord within an opening provided in housing front panel 25 through the use of an appropriate fitting 26. Ideally the end of cord 22 terminates at a distance spaced from the front of lamp 14 corresponding to the focal length of the lamp so that a maximum amount of the light from the lamp is transmitted through cord 22.

The light transmitted through cord 22 is directed to the desired location by a contra angle probe 27 mounted on the end of a manually held handle 28 secured to the adjacent end of cord 22. Probe 27 is attachable to handle 28 by a connection collar 30 having internal threads, not shown, for attachment to the handle.

The frequency range of the light emitted from probe 27 is regulated by a filter 18 disposed within a cylindrical cap 32 having internal threads for detachable engagement of the cap with the associated end of probe 27. As illustrated in FIG. 2, filter 18 is formed in a disc shape and is held in place within cap 32 by an internal shoulder 34 bearing against the front side of the filter and a retaining ring 36 pressed against the rear side of the filter. The outer diameter of retaining ring 36 is sized to produce a tight interference fit with the interior of cap 32. It will be appreciated that by this construction, filter 18 may be removed and replaced by other filters tuned to allow passage of different frequencies of light by simply unscrewing cap 32 from probe 27 and replacing it with another cap and associated filter.

In a preferred form of the present invention, filter 18 is composed of a dichroic filter lens which is capable of effectively filtering out unwanted light frequencies while minimizing the attenuation of the desired band width spectra. The dichroic lens is manufactured by applying an aluminized coating to silicon glass in a vacuum chamber. The types of gases used in the coating process and the thickness of the coating determine the frequency range of the light which is allowed to pass through the lens.

Applicant has found that for a particular commercial brand of organic composite material used to restore teeth, there is an optimum light frequency range which thoroughly and quickly cures the composite material. As illustrated in FIG. 3, this was determined by utilizing a grading monochromator 40 to produce light at one frequency at a time. The light generated by the monochromator was directed to a sample of the composite material 42 held between two layers of silicon glass. The silicon glass was used to avoid absorption of significant amounts of light in the ultraviolet and near ultraviolet frequency ranges. The light refracted from the sample material was analyzed by a photometer 44 to determine the intensity and frequency of the light absorbed by the sample material during polymerization. This data may be visually displayed by an appropriate apparatus 46, such as on an oscilloscope or a strip chart recorder. By this method, the precise light frequency range initiating polymerization of the polymer and monomer composing the composite binder was measured and plotted.

Once the optimum frequency range at which curing of the restorative material occurs has been thusly determined, a dichroic lens, such as lens 18, may be produced to filter out substantially all wave lengths of light except that of the optimum frequency range. As discussed above, the operational characteristics of the dichroic lens are controlled by proper choice of the gases used in the aluminum coating process and by controlling the thickness of the aluminum coating deposited on the silicon glass. The dichroic lens attenuates substantially all of the light of unwanted frequencies including near infrared and ultraviolet light which may be harmful to the patient. Moreover, the ultraviolet light has been found to cause instability of the restorative material by inducing substantial cross-linking of the resin molecules. The dichroic lens also attenuates wavelengths of light which generate substantial amounts of heat, i.e. above 700 nanometers, to prevent incomplete or non-uniform curing of the composite caused by preventing oxides generated during the polymerization process from flashing off of the composite.

It will be appreciated that by the above procedure, apparatus 10 not only can be conveniently tuned to generate light in the desired frequency range for all commercially available dental restorative composites, but also can be employed to efficiently and fully cure composite materials developed in the future. As a consequence, apparatus 10 has a useful service life which is substantially longer than known optical curing units.

As will be apparent to those skilled in the art to which the invention is addressed, the present invention may be embodied in forms or carried out in steps other than those specifically disclosed above without departing from the spirit or essential characteristics of the invention. The particular embodiment of a generating apparatus 10 and the particular steps used to carry out the present invention, as described above, are therefore to be considered, in all respects, as illustrative and not restrictive, with the scope of the present invention being set forth in the appended claims rather than being limited to the foregoing description.

What is claimed:

1. An apparatus for applying light in selective frequency ranges to organic composite materials used in restorative dentistry for optimum curing of the composite materials, comprising:
   light bulb means;
   means for energizing said light bulb means;
   and filter means selected with reference to the composition of the composite material to be cured and used to attenuate substantially all frequencies of light produced by said light bulb means except the frequency range which produces uniform curing of the composite material without causing radical cross-linking of the composite material; and
   further comprising a flexible, light transmitting cord means having a first end in light transmission communication with said light means and means for detachably mounting said filter means on the end portion of said light cord means distal from said light means.

2. The apparatus according to claim 1, wherein said light bulb means comprises a quartz halogen lamp.

3. The apparatus according to claim 1, wherein said filter means includes a dichroic filter lens selected to substantially filter out all frequencies of light produced by said light means except those frequencies which are highly absorbed by the composite material being cured.

4. The apparatus according to claim 1, wherein said mounting means comprises a lens cap detachably engagable with the light cord means, said lens cap having a substantially hollow interior for receiving said dichroic filter lens.

5. An apparatus for photochemically curing organic composite materials used in restorative dentistry, comprising:
   light bulb means;
   means for energizing said light bulb means;
   flexible cord means for transmitting light generated by said light bulb means to a desired location; and
   filter means mounted on the end of said cord means distal from said light bulb means, said filter means selected with reference to the composition of the composite material to be cured and used to filter the light generated by said light bulb means to allow substantially only light of a frequency range producing uniform and complete curing of the composite material without causing radical cross-linking of the composite material.

6. The apparatus according to claim 5, wherein said filter means includes a dichroic filter lens selected to substantially filter out all frequencies of light produced by said light bulb means except those frequencies which are highly absorbed by the composite material being cured without causing radical cross-linking of the composite material.

* * * * *